US00PP16905P3

(12) United States Plant Patent
Jensen

(10) Patent No.: US PP16,905 P3
(45) Date of Patent: Aug. 1, 2006

(54) MINIATURE ROSE PLANT 'JENTWO'

(50) Latin Name: *Rosa hybrida*
Varietal Denomination: JENtwo

(75) Inventor: Svend Jensen, Christiansfeld (DK)

(73) Assignee: Cal Europe, Santa Barbara, CA (US)

( * ) Notice: Subject to any disclaimer, the term of this patent is extended or adjusted under 35 U.S.C. 154(b) by 71 days.

(21) Appl. No.: 10/848,786

(22) Filed: May 19, 2004

(65) Prior Publication Data

US 2005/0262599 P1 Nov. 24, 2005

(51) Int. Cl.
*A01H 5/00* (2006.01)

(52) U.S. Cl. ..... Plt./122

(58) Field of Classification Search ..... Plt./116, Plt./122, 123, 129
See application file for complete search history.

(56) References Cited

U.S. PATENT DOCUMENTS

PP9,635 P * 8/1996 Pouw ..... Plt./122

* cited by examiner

*Primary Examiner*—Howard J. Locker
(74) *Attorney, Agent, or Firm*—Linek Yankelevitz Sunshine & Regenstreif

(57) ABSTRACT

A new miniature rose plant which has abundant, long lasting, dark-red colored flowers and attractive semi-glossy foliage. The variety successfully propagates from softwood cuttings and is suitable for year round production in commercial glass houses as a flowering pot plant. This new and distinct variety has shown to be uniform and stable in the resulting generations from asexual propagation.

2 Drawing Sheets

Figures 1, 2, 3, 4, 5, 6, 7, 8, 9:
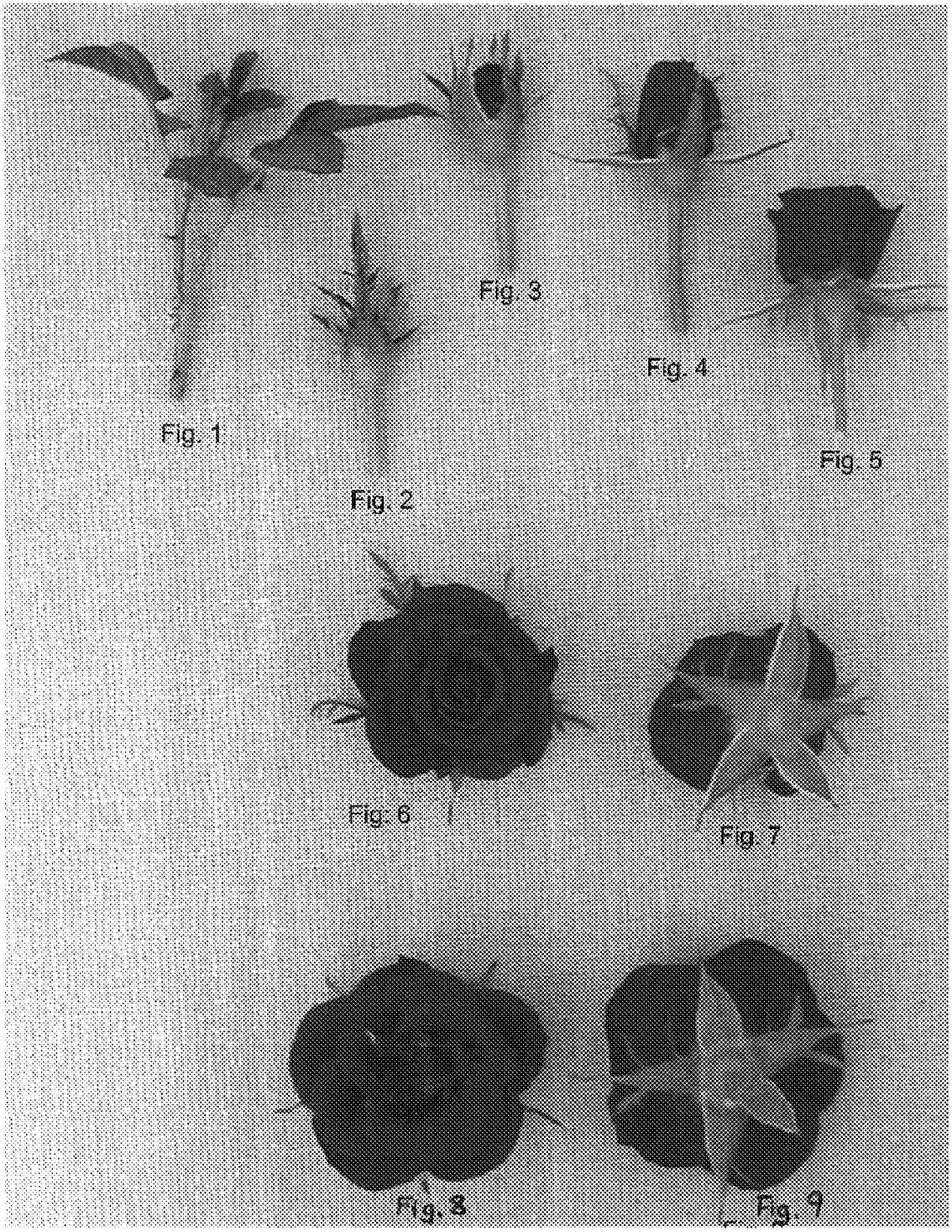

Latin name of genus and species: *Rosa hybrida* 'JENtwo.'
Variety denomination: The new variety is named 'JENtwo'.

BACKGROUND OF THE INVENTION

The present invention constitutes a new and distinct variety of miniature rose plant, which was developed by artificially pollinating an unnamed seedling (not patented in the US) with an unnamed seedling (also not patented in the US). The two parents were crossed during the summer of 2001, and the resulting seed was sown in December 2001, in a controlled glasshouse environment. Out of the resulting seedlings one seedling was selected, as a distinct new variety and was named JENtwo. The variety can be distinguished from its seed parent, an unnamed seedling, by the following combination of characteristics:

- JENtwo has small double flowers, while the unnamed seed parent has medium sized single flowers.
- JENtwo has dark-red colored petals, while the unnamed seed parent has orange petals.

The new variety may distinguished from its pollen parent, an unnamed seedling created by the same inventor, by the following combination of characteristics:

- JENtwo has smaller flowers and foliage as compared to the unnamed pollen parent.
- JENtwo has dark-red colored petals, while the unnamed pollen parent has white petals.

BRIEF SUMMARY OF THE INVENTION

Initial asexual reproduction of JENtwo by cuttings was first carried out by the inventor in Christiansfeld, Denmark. The reproduction was conducted under controlled greenhouse conditions. Having demonstrated asexual reproduction it was found that all characteristics and distinctions came true to form and were established in succeeding propagations. JENtwo is a low and compact miniature rose with medium vigor. Tests show that the life for the entire plant and for a single flush of flowers is medium as compared to similar varieties.

The objective of the hybridization of this rose variety for commercial greenhouse culture was to create a new and distinct variety with:

- Uniform and abundant flowers with good keeping properties;
- Attractive long lasting foliage and overall compact growth, and young foliage has striking red edges;
- Year round flowering under glasshouse conditions;
- Suitably for production from softwood cuttings in pots; and
- Durable flowers and foliage which make the variety suitable for distribution in the floral industry.

This combination of qualities was not present in previously available commercial cultivars of this type and distinguishes JENtwo from all other varieties of which we are aware. The seeds from hybridization were planted in a controlled environment and evaluations were conducted on the resulting plants. JENtwo was selected by Svend Jensen, in his development program in Christiansfeld, Denmark.

BRIEF DESCRIPTIONS OF THE DRAWINGS

The accompanying color illustrations show as true as is reasonably to obtain in color photographs of this type, the typical characteristics of the buds, flowers, leaves, stems of 'JENtwo'. Specifically illustrated in:

Photo sheet #1:

FIG. 1 Young shoot.

FIG. 2 Bud before opening the sepals.

FIG. 3 Bud at the stage opening the sepals.

FIG. 4 Bud at the stage opening the petals.

FIG. 5 Flower during course of opening.

FIG. 6 Open flower—plan view—obverse.

FIG. 7 Open flower—plan view—reverse.

FIG. 8 Fully open flower—plan view—obverse.

FIG. 9 Fully open flower—plan view—reverse.

Figures 10, 11, 12, 13, 14, 15, 16, 17, 18:
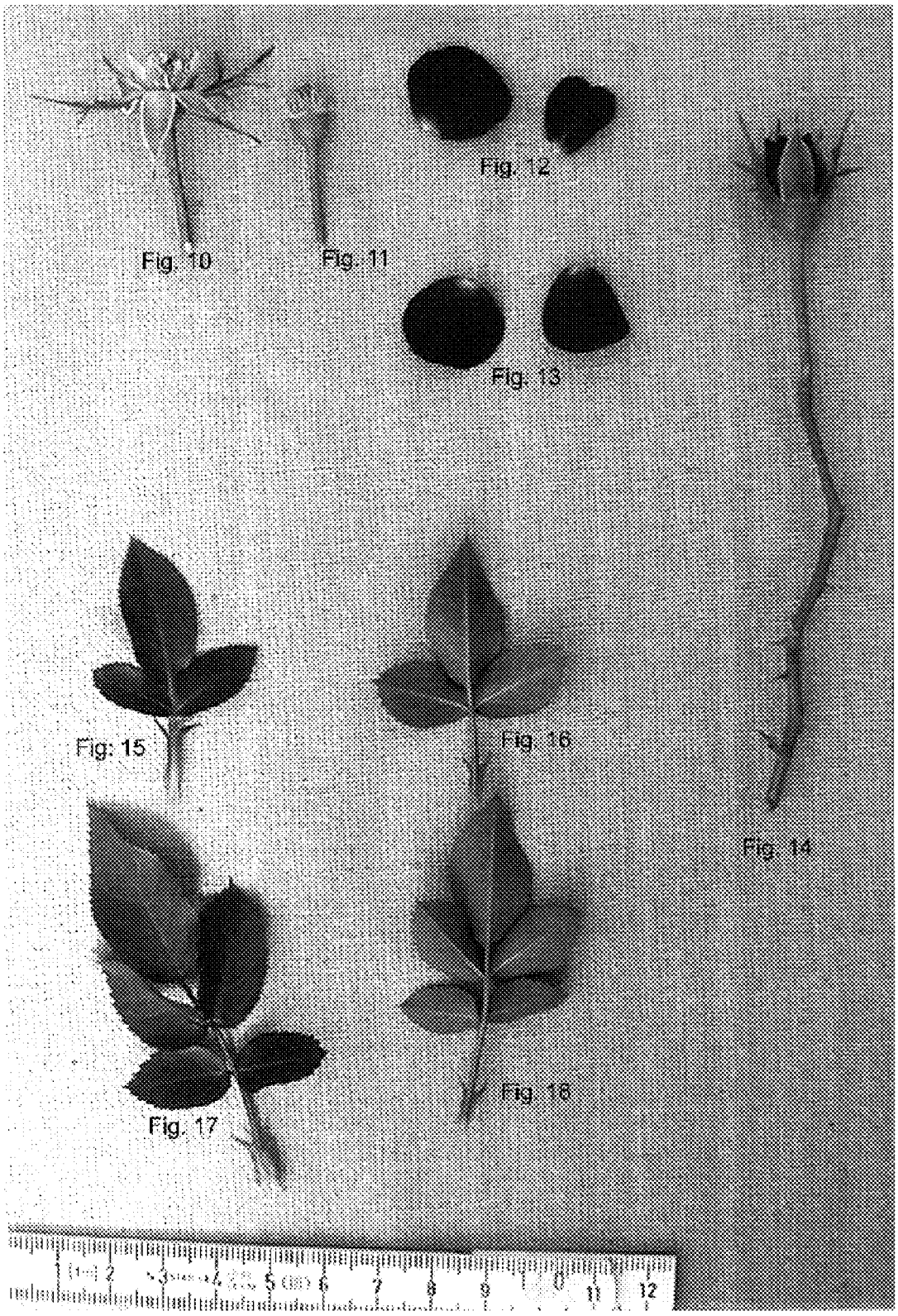

Photo sheet #2:

FIG. 10 Receptacle showing stamens and pistils.

FIG. 11 Receptacle showing pistils (stamens and sepals removed).

FIG. 12 Flower petals, detached—Inner surface.

FIG. 13 Flower petals, detached—Outer surface.

FIG. 14 Bare stem exhibiting thorns and flower attachment.

FIG. 15 Three leaflets upper side.

FIG. 16 Three leaflets reverse side.

FIG. 17 Five leaflets upper side.

FIG. 18 Five leaflets reverse side.

DETAILED BOTANICAL DESCRIPTION OF THE VARIETY

The following is a detailed description of the Miniature Rose: *Rosa hybrida* 'JENtwo'. The following observations, measurements, values and comparisons describe plants grown in glass houses in Christiansfeld, Denmark. The age of the observed plants was 11 to 13 weeks after propagation by cuttings, and growth as flowering pot plants in containers 10 centimeters in diameter. Color references are made using The Royal Horticultural Society (London, England) Colour Chart, 1995, except where common terms of color are used.

For a comparison, the nearest existing rose variety is 'Ruijef', a rose variety described and illustrated in U.S. Plant Pat. No. 9,635.

Chart I details several physical characteristics of JENtwo and Ruijef.

| Chart 1: | JENtwo | Ruijef |
|---|---|---|
| Petal color, Upper surface | Red Group 46A | Red Group 46A |
| Petal color, Reverse surface | Red Group 46A | Red Group 59B |
| Petal count | 20 | 35–45 |

Parents: Unnamed seedling. Times. Unnamed seedling.
Classification:
Botanical: *Rosa hybrida.*
Commercial: Miniature.
Plant:
Plant growth: Moderately vigorous. Grows compact upright to bushy. When grown as 10 cm pot plant, the average height of the plant itself is 18 to 20 cm, and average width is 20 cm. When grown as a 15 cm pot plant, the average height of the plant itself is 22 to 27 cm, and average width is 30 cm.

Production time is generally 11 to 13 weeks depending on average temperature, light level, and cultural practices.

Stem:
*Color.*—Young wood: Yellow-Green Group 153 D. Older wood: Yellow-Green Group 152 B.
*Thorns.*—Incidence: High number of thorns. Size: 3–6 mm. Color: Green-White Group 157D grading to Red Group 53A at the tip. Shape: Deep concave.
*Surface.*—Young wood: Smooth. Older wood: Smooth:
*Stem diameter.*—3–4 mm.
*Internode length.*—20–30 mm.
*Numbers of internodes.*—6–8.

Plant foliage: Leaves arranged alternately, compound with 3, 5 7 leaflets per leaf, generally symmetrical, abundant, and flat in aspect. Stipules at petiole base.
*Quantity of leaves.*—6–8 per lateral branch.
*Leaf size.*—Medium 60–80 mm (length). times. 30–40 mm(width), for 5 leaflet.
*Petioles.*—Color: Yellow-Green Group 148A–C, Margins: with small prickles Red Group 53A. Length: 8–10 mm Diameter: about 1–2 mm.
*Stipules.*—Size: 6–10 mm. Surface: Smooth. Color: Yellow-Green Group 147A, With intonations of Greyed-Purple Group 185B. Margins: serrated, single.
*Rachis.*—Color: Yellow-Green Group 148A–C, With intonations of Greyed-Purple Group 185B. Margins: With small pickles, Red Group 53 A. Length: 25 to 30 mm.
*Leaflets.*—Edge: Serrated. Serration: Double. Shape: Ovate with acute apex and obtuse base. Texture: Smooth. Appearance: Upper surface: semi-glossy; Lower surface: dull. Size: 18–35 mm (length) and 8–18 mm (width). Color: Young foliage: Upper surface: Greyed-Red Group 181A. Lower surface: Greyed-Red Group 180A. Color: Mature foliage: Upper surface: Green Group 147A. Lower surface: Greyed-Green Group 191A. With intonations of Greyed-Red Group 181B.

Inflorescence:
*Blooming habit.*—Recurrent.
*Number of flowers.*—Generally 1–3 bud per flowering stem.
*Peduncle.*—Color: Yellow-Green Group 152B, Texture: Smooth, with stipitate glands. Length: 20–25 mm. Strength: Upright.
*Receptacle.*—Surface: Smooth, glabrous. Shape: Cupped-shaped. Size: h: 5–6 mm. w: 6–8 mm. Color: Yellow-Green Group 147B.
*Sepals.*—Quantity: 5. Shape: Narrowly Ovate w. acute tip. Texture: Leathery. Margin: Foliaceous appendages on 3 of the five sepals. Appearance: Dull. Color: Upper surface: Yellow-Green Group 147A–B. Reverse surface: Greyed-Green Group 191A.
*Buds.*—Size (during opening): 15–18 mm in height and 10–12 mm in width. Shape: Narrowly ovoid and blunt. Color: at ¼ opening, Red Group 46 A.
*Flower.*—Duration of entire flush: 18 to 21 days. Fragrance. None. Size: 40–45 mm in diameter. Form: Shape of lower when viewed from the side, Opening: Cup-shaped. Fully open: Saucer-shaped. Color: Petals, upon opening. Upper surface: Red Group 46A. Reverse surface: Red Group 46A. Petals after opening: Upper surface: Red Group 46 A. Reverse surface: Red Group 46A. Basal Petals spots: Size: 1–2 mm. Color: White Group 155D. General tonality: On Open flower: Third day: Red Group 46A. Afterwards: Red Group 46B. Petals: Petal reflex. Outermost petals reflex backwards at opening. Fully open all petals reflex backwards. Texture. Smooth. Petal edge. Uniform. Petal count. Approximately 20 on the average per flower. Petal size. Length 13–15 mm Width: 10–20 mm. Shape. Outer petals: Round. Inner petals: Ovate. Reproductive organs: Stamen number: Approximately 40 an average per flower. Pollen. Color: Yellow-Orange Group 220, Abundance: Average. Anthers. Size: 1–2 mm; Color: White Group 155D; Shape Oblong. Filaments. Size: 4–5 mm Color: Yellow-Orange Group 20D. Pistils number: Approximately 20 on average per flower. Stigmas. Location: Under in location to anthers. Color: Green-White Group 157D. Styles. Color: Red Group 53A. Length: 2 to 4 mm.

Development:

*Vegetation.*—Dense.

*Blooming.*—Abundant.

*Aptitude to bear fruit.*—Poor.

*Resistance to diseases.*—Above average resistance to mildew and Botrytis under normal growing conditions in Christiansfeld, Denmark.

Hips/seeds has not been observed due to that the plant has never been grown to the stage of seed development, due to the fact, that the variety is developed for use as a flowering pot plant only.

Winter hardiness & drought/heat tolerance: Due to the fact, that this variety is a potted flowering plant, developed for one time use only(indoor houseplant), the plant is not tested for winter hardiness or drought/heat tolerance.

What is claimed is:

1. A new and distinct variety of rose plant of the miniature class, substantially as herein illustrated and described as a distinct and novel rose variety due to its abundant, long lasting, dark-red colored flowers, attractive long lasting semi-glossy foliage, vigorous and compact growth, year round flowering under glasshouse conditions, suitability for production from softwood cuttings in pots, and durable flowers and foliage which make the variety suitable for distribution in the floral industry.

* * * * *